(12) United States Patent
Makino (10) Patent No.: US 7,325,923 B2
(45) Date of Patent: Feb. 5, 2008

(54) OPHTHALMIC EXAMINATION AND TREATMENT SYSTEM

(75) Inventor: Toshimi Makino, Tokyo (JP)

(73) Assignee: Makino Ophthalmic Instrument Co., Ltd., Tokyo (JP)

( * ) Notice: Subject to any disclaimer, the term of this patent is extended or adjusted under 35 U.S.C. 154(b) by 651 days.

(21) Appl. No.: 10/787,180

(22) Filed: Feb. 27, 2004

(65) Prior Publication Data

US 2005/0195359 A1 Sep. 8, 2005

(51) Int. Cl.
  *A61B 3/10* (2006.01)
  *A61B 3/00* (2006.01)
  *A61B 3/14* (2006.01)

(52) U.S. Cl. ............... 351/205; 351/200; 351/206; 351/212; 351/214; 351/221; 382/115

(58) Field of Classification Search ........... 351/200, 351/205, 206, 209, 210, 212, 214, 218, 221, 351/246, 247; 128/645, 745; 606/4–6; 382/115, 382/117; 348/61, 77, 78
See application file for complete search history.

(56) References Cited

U.S. PATENT DOCUMENTS

| | | | | |
|---|---|---|---|---|
| 4,662,731 A | * | 5/1987 | Robert et al. | 351/214 |
| 5,098,426 A | * | 3/1992 | Sklar et al. | 606/5 |
| 5,455,644 A | * | 10/1995 | Yazawa et al. | 351/206 |
| 5,528,323 A | * | 6/1996 | Fujieda et al. | 351/218 |
| 5,830,147 A | * | 11/1998 | Feke et al. | 600/479 |
| 5,993,001 A | * | 11/1999 | Bursell et al. | 351/212 |
| 6,761,455 B2 | * | 7/2004 | Sumiya | 351/221 |
| 7,123,751 B1 | * | 10/2006 | Fujieda | 382/115 |
| 7,147,328 B2 | * | 12/2006 | Sugino et al. | 351/206 |
| 2003/0007126 A1 | * | 1/2003 | Sekiguchi | 351/206 |
| 2003/0035084 A1 | * | 2/2003 | Makino | 351/205 |

* cited by examiner

*Primary Examiner*—Loha Ben
(74) *Attorney, Agent, or Firm*—Oblon, Spivak, McClelland, Maier & Neustadt, P.C.

(57) ABSTRACT

An ophthalmic examination and treatment system including ophthalmic medical instruments, wireless imaging devices mounted on the ophthalmic medical instruments, and one or more display devices for displaying images captured with the imaging devices. Each imaging device includes transmission/reception unit for transmission and reception of information data with the display device by wireless communication. The transmission/reception unit has an ID allocated correspondingly to each imaging device, transmits a data signal with the ID signal to the transmission/reception unit, and when an ID confirmation signal attached to a control signal from the transmission/reception unit and the own ID coincide, receives the control signal. The display device receives a data signal with an ID signal from each imaging device, conducts displaying with the data signal corresponding to the ID and enables the remote control of the imaging device corresponding to the ID by attaching the ID signal and sending the control signal.

12 Claims, 6 Drawing Sheets

OPHTHALMIC EXAMINATION AND TREATMENT SYSTEM

BACKGROUND OF THE INVENTION

1. Field of the Invention

The present invention relates to a medical instrument, more specifically, an ophthalmic medical instrument to be used in ophthalmic examination and treatment, and particularly to an ophthalmic examination and treatment system equipped with a wireless imaging device and a display device for displaying the captured images thereof.

2. Description of the Related Art

For example, slit lamps and operation microscopes used in ophthalmic surgery (they are also used in brain surgery) and fundoscopy devices are well known as ophthalmic medical instruments employed during ophthalmic examination and treatment. In those medical instruments, an imaging device is installed permanently or optionally, and this imaging device is used for imaging the condition of the affected area and the state of treatment, and displaying those condition and state on a monitor screen which is a display device provided separately.

A CCD camera has been employed as the aforementioned imaging device in this type of ophthalmic medical instrument, but there is a problem in that a wire-type system where the camera and the display device are connected with a cable is generally employed, making the instrument difficult to use. Thus, when the aforementioned imaging device is attached to a part of the ophthalmic medical instrument which is the primary instrument, it is necessary to provide a cable for transmitting the images from the imaging device to a display device or the like. Moreover, even upon installing the imaging device in a position in the vicinity of the object to be imaged, since this location is also an important section for the primary instrument, the installation position is easily restricted and cases arise where only such installation is possible in which adequate imaging is difficult.

Moreover, although this is not a serious problem when the aforementioned ophthalmic medical instrument is fixedly installed in an ophthalmic examination room or operating room, a problem arises when the instrument is used as a transportable system in a traveling clinic or the like. In particular, since each ophthalmic medical instrument has primary portions with functions inherent thereto, such primary portions also have multiple power cables and transmission cables. Thus, when there were additional cables for the imaging device, the handling thereof became complicated and the cables were sometimes a hindrance during transportation.

Accordingly, the applicant has previously suggested an ophthalmic examination and treatment system using a wireless CCD camera for the aforementioned ophthalmic medical instrument (for example, Japanese Utility Model Registration No. 3084145).

Significant advantages of such an ophthalmic examination and treatment system are that the wireless CCD camera can be installed in an appropriate position of the instrument, good user friendliness thereof is demonstrated, and an image picked up with the camera can be displayed on a freely installed display device.

Furthermore, there are also ophthalmic examination and treatment systems in which charts produced by handwriting or by a PC input during diagnostics by doctor are converted into electronic format so that they can be displayed on a display device by using the aforementioned wireless CCD camera (for example, Japanese Utility Model Registration No. 3084146).

Such an ophthalmic examination and treatment system has a significant advantage because it can provide a simple and inexpensive chart management system.

However, in a communication system using wireless communication between the aforesaid wireless CCD camera and a display device receiving the image data signals transmitted from the camera, if the number of cameras or display devices is increased, the system structure becomes complex and there is also a risk of wires getting crossed. Accordingly, certain measures have to be taken.

Thus, if a plurality of the above-described ophthalmic examination and treatment systems are installed, the number of cameras is increased and the number of display devices also increases. Sharing the display devices can be also considered, but if they operate at the same time, transmission and reception of image data using wireless communication between a camera and a corresponding display device becomes unstable.

For this reason, in the ophthalmic examination and treatment systems of this type, certain measures have to be taken to improve user friendliness of the wireless imaging devices mounted on a plurality of ophthalmic medical instruments, to simplify the relationship with the corresponding display device, recording device, or the like, and to improve the overall convenience thereof.

SUMMARY OF THE INVENTION

The present invention was devised in view of the foregoing circumstances, and an object thereof is to enable adequate and reliable system management in an ophthalmic examination and treatment system composed of a wireless imaging devices installed on medical instruments of various types to be used in ophthalmic examination and treatment and display devices for displaying images picked up by the imaging devices.

In order to achieve the foregoing object, an ophthalmic examination and treatment system according to an embodiment of the present invention comprises: a plurality of ophthalmic medical instruments used in ophthalmic examination and treatment; a wireless imaging device mounted on each of the ophthalmic medical instruments; and at least one display device for displaying images captured with the imaging devices, wherein each imaging device comprises transmitting and receiving units conducting transmission and reception of information data with the display device by wireless communication, the transmission/reception unit has an inherent ID allocated corresponding to each imaging device, transmits a data signal to the transmission/reception unit of the display device with the ID signal attached thereto and when an ID confirmation signal attached to a control signal from the transmission/reception unit of the display device and the own ID coincide, receives the control signal, and the display device receives a data signal with an ID signal attached thereto from each imaging device, conducts displaying with the data signal corresponding to the ID and enables the remote control of the imaging device corresponding to the ID by sending a control signal with the ID signal attached thereto.

In an ophthalmic examination and treatment system according to another embodiment of the present inventions, the ophthalmic examination and treatment system described above has a display device which comprises a recording device for recording the image displayed on the display device.

In an ophthalmic examination and treatment system according to yet another embodiment of the present invention, the ophthalmic medical instrument described above is any of a slit lamp, an operation microscope, a fundoscopy device, or a display instrument for displaying a chart produced by a doctor by handwriting or a PC input.

In an ophthalmic examination and treatment system according to still another embodiment of the present invention, the imaging device described above is a wireless CCD camera.

In accordance with the present invention, when a plurality of ophthalmic medical instruments are used in combination, employing a configuration in which wireless communication between wireless imaging devices mounted on respective instruments and a display device conducting display of the image data thereof is conducted by using an ID number allocated in advance to each imaging device makes it possible to conduct displaying from a prescribed imaging device in a prescribed state, without causing wire crossing or the like.

As described hereinabove, with the ophthalmic examination and treatment system in accordance with the present invention, when a plurality of ophthalmic medical instruments are used in combination, employing a configuration in which wireless communication between wireless imaging devices mounted on respective instruments and a display device conducting display of the image data thereof is conducted by using an ID number allocated in advance to each imaging device makes it possible to conduct displaying from a prescribed imaging device adequately and accurately, without causing wire crossing or the like, and a simple and inexpensive ophthalmic examination and treatment system can be provided.

In particular, in accordance with the present invention, the advantages that are due to the utilization of a wireless imaging devices, such as freedom in selecting the installation position, transition to adequate captured images, and freedom of instrument transportation can be demonstrated to a greater degree.

DESCRIPTION OF THE PREFERRED EMBODIMENTS

Figure 1:
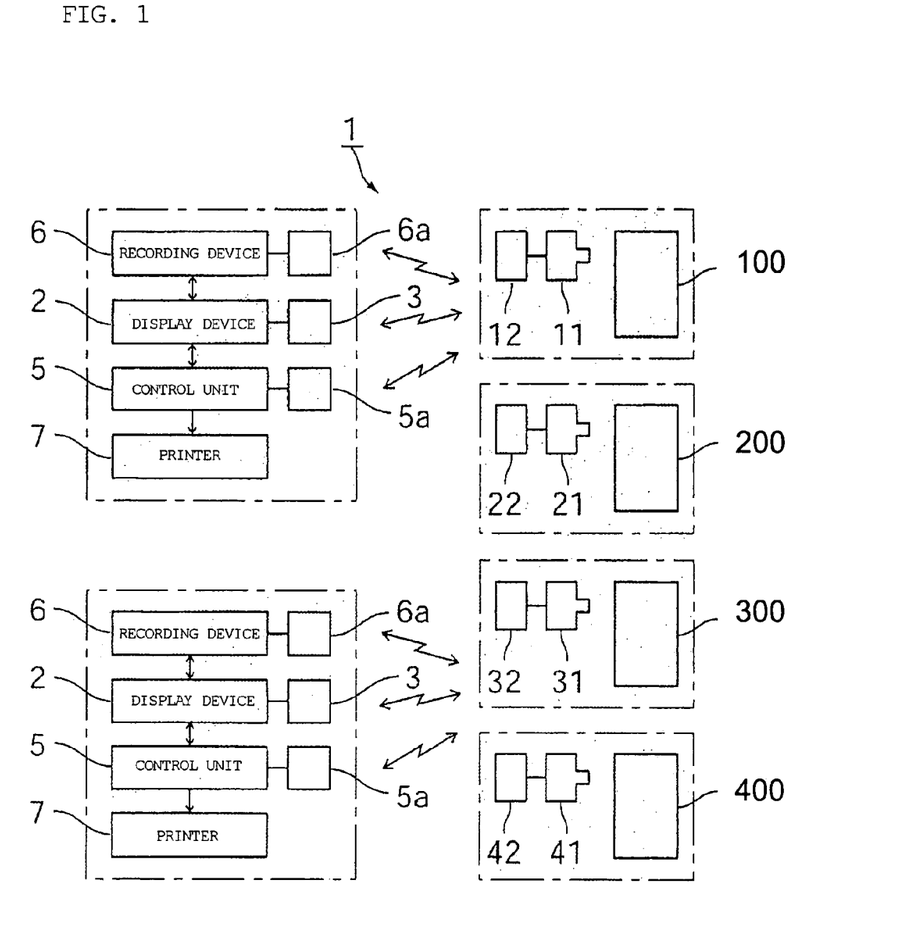
FIG. 1 is an explanatory diagram for showing an embodiment of the ophthalmic examination and treatment system according to the present invention, and explaining the overall description thereof.

FIG. 1 illustrates an embodiment of the ophthalmic examination and treatment system in accordance with the present invention. The overall ophthalmic examination and treatment system is represented with reference numeral 1 and comprises various ophthalmic medical instruments (assigned with reference symbols 100, 200, 300, 400) such as a slit lamp 100, an eyepiece of a slit lamp 200 or a fundoscopy device, all described hereinbelow, used in ophthalmic diagnosis, imaging devices 11, 21, 31, 41 composed of wireless CCD cameras mounted on the ophthalmic medical instruments 100, 200, 300, 400; and display devices 2 (here, two devices are used) for displaying the images captured with those imaging devices 11, 21, 31, 41.

In the present embodiment two display devices 2 are used. The reference numeral 5 in the figure stands for a control unit used when manually operating the aforementioned display devices 2 and also the imaging devices 11, 21, 31, 41. The reference numeral 6 stands for a recording device for directly recording images obtained with the devices 11, 21, 31, 41, or indirectly recording, via the display devices 2, the images displayed on the display devices 2. Each of these devices 2, 5 and 6 is respectively provided with a transmission/reception unit 3, 5a and 6a for transmitting and receiving signals to and from the transmission/reception units 12, 22, 32, 42 of the imaging devices 11, 21, 31, 41 (for example, provided on the rear end portion of the cameras). Further, a printer 7 capable of outputting a display image as necessary may be also provided.

In accordance with the present invention, in the overall ophthalmic examination and treatment system 1 using the aforementioned wireless imaging devices 11, 21, 31, 41 (wireless CCD cameras) and configured so that transmission and reception of information data with at least one display device 2 are conducted by wireless communication, the imaging devices 11, 21, 31, 41 are provided with transmission/reception units 12, 22, 32, 42 for conducting transmission and reception of information data with the display device 2 by wireless communication.

Further, those transmission/reception units 12, 22, 32, 42 have inherent ID allocated correspondingly to respective imaging devices 11, 21, 31, 41, a data signal having the ID signal attached thereto is transmitted, e.g., to the transmission/reception unit 3 of the display device 2, and when the ID confirmation signal attached to the control signal from the transmission/reception unit 3 of the display device 2 (or it may be a transmission/reception unit 5a of control unit 5) and the own ID match, the control signal is received. Furthermore, the display device 2 comprises the transmission/reception unit 3 for receiving a data signal having an ID signal attached thereto from respective imaging devices 11, 21, 31, 41, conducts displaying according to the data signal corresponding to the ID, and sends a control signal with an ID signal attached thereto, thereby enabling remote control of the imaging device 11, 21, 31, 41 corresponding to the ID.

Figure 2:
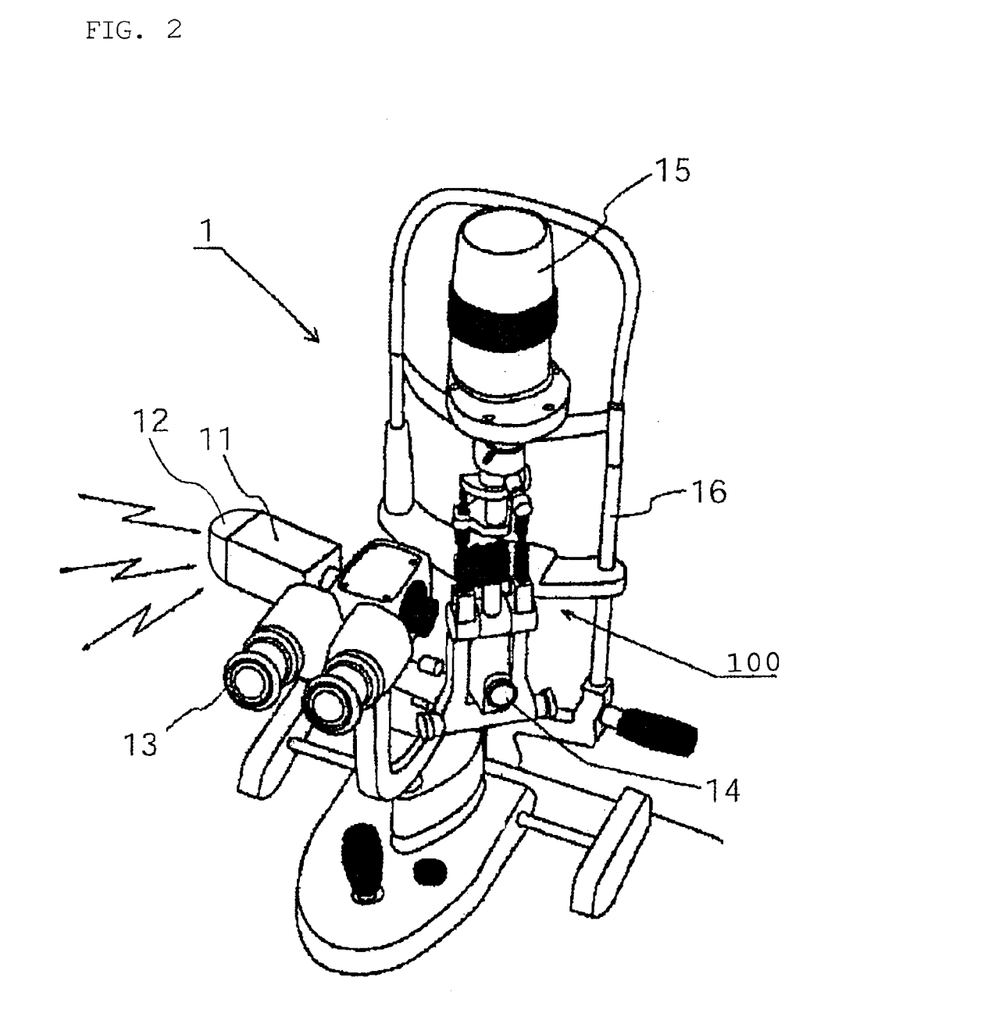
FIG. 2 is a schematic perspective view of a slit lamp as an example of the ophthalmic medical instrument to which the ophthalmic examination and treatment system according to the present invention is applied.
Figure 3:
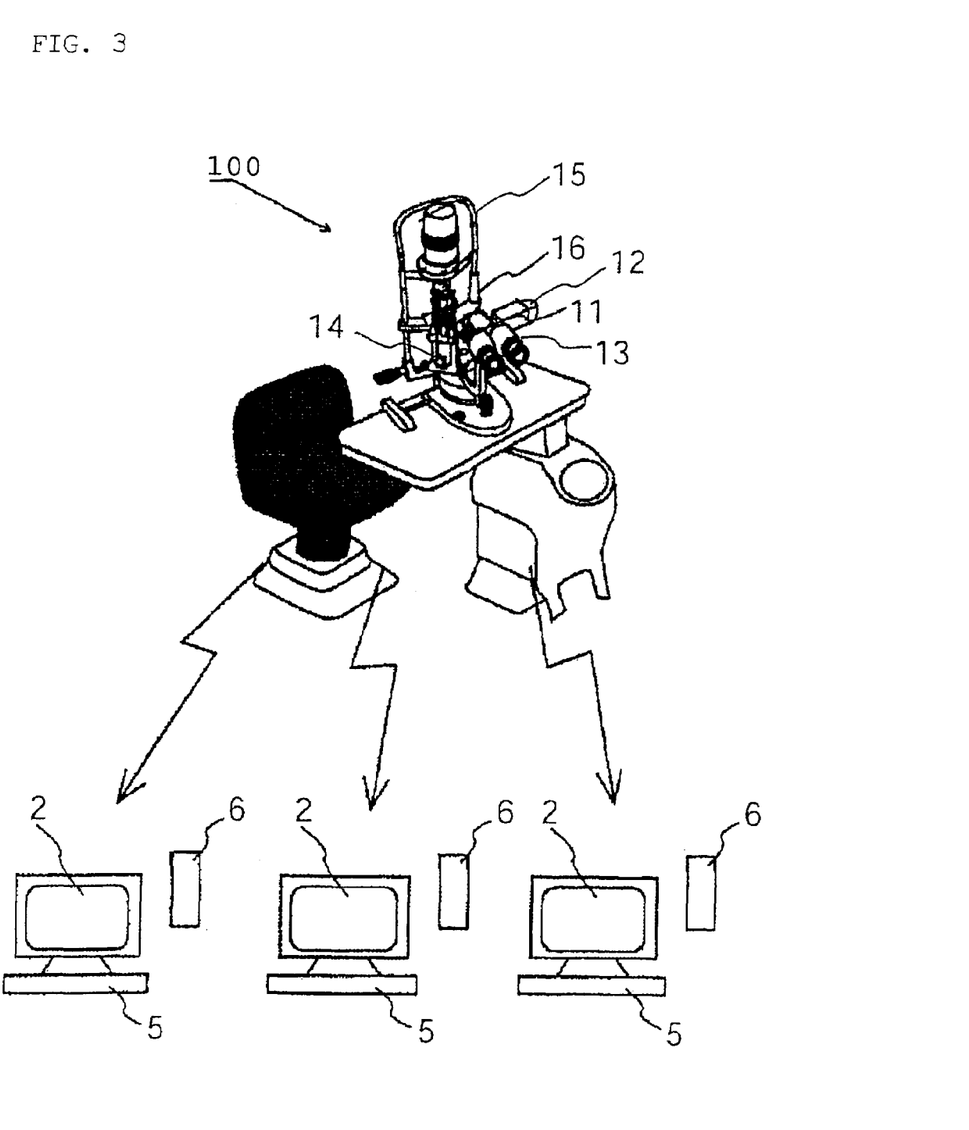
FIG. 3 is an explanatory view for explaining the outline of the ophthalmic examination and treatment system employing the slit lamp shown in FIG. 2.
Figure 4:
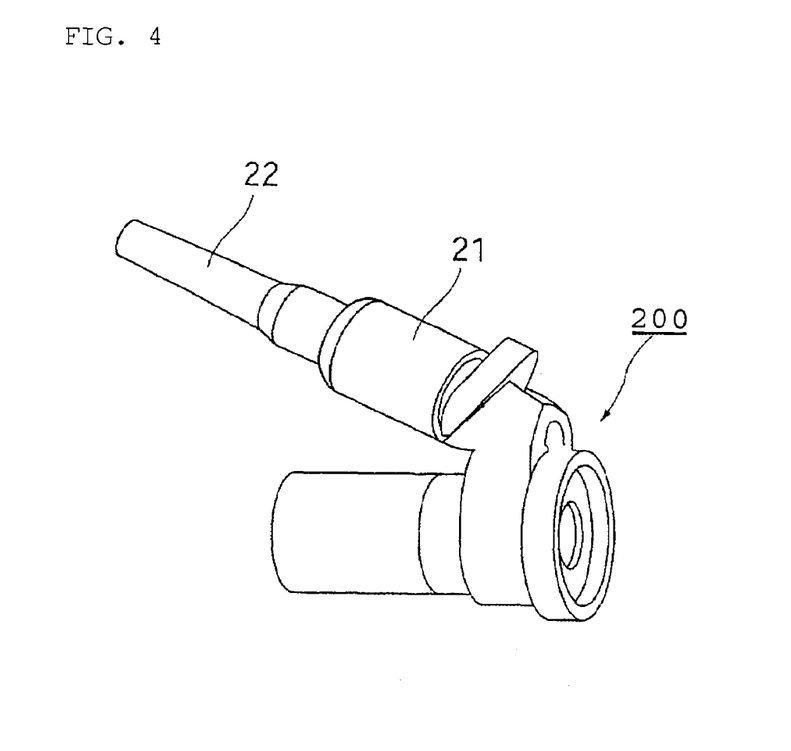
FIG. 4 is a schematic view illustrating an example of an eyepiece of a slit lamp.
Figure 5:
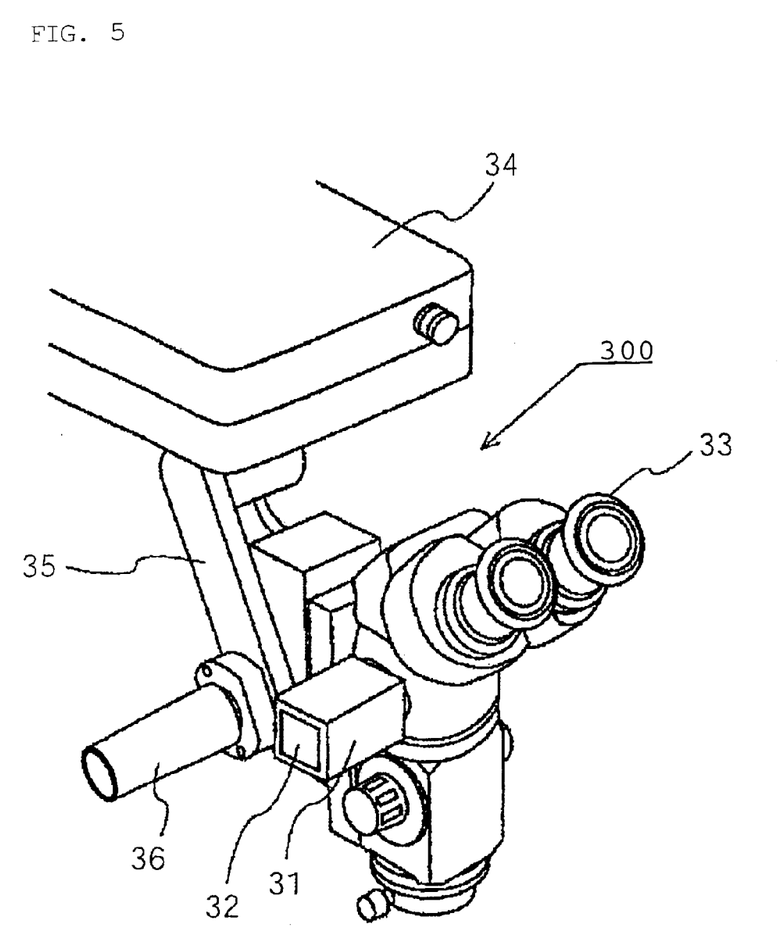
FIG. 5 is a schematic perspective view of an operation microscope as an example of the ophthalmic medical instrument to which the ophthalmic examination and treatment system according to the present invention is applied.
Figure 6:
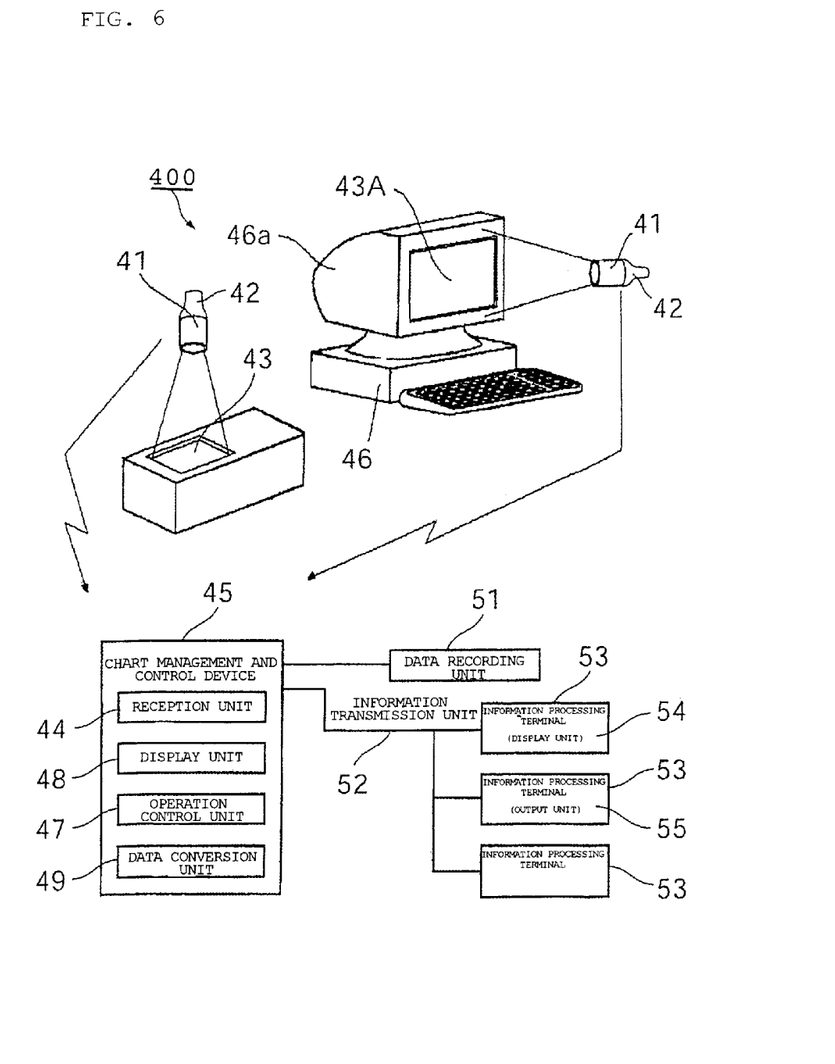
FIG. 6 is a schematic perspective view of a chart management system as an example of the ophthalmic medical instrument to which the ophthalmic examination and treatment system according to the present invention is applied.

Here, instruments conventionally known to be widely used for ophthalmic diagnosis, such as slit lamp 100, eyepiece of a slit lamp 200 as shown in FIGS. 2, 3, and 4, an operation microscope 300 as shown in FIG. 5, and a fundoscopy device, or an instrument used as a chart management system comprising a display device for displaying a chart produced by a doctor by handwriting or by a PC input, such chart being shown in FIG. 6, may be used as the aforementioned ophthalmic medical instrument.

With the ophthalmic examination and treatment system 1 of the above-described configuration in which ophthalmic medical instruments 100, 200, 300, 400 are equipped with wireless imaging devices 11, 21, 31, 41, when a plurality of ophthalmic medical instruments 100, 200, 300, 400 are used in combination, employing a configuration in which wireless communication between the wireless imaging devices 11, 21, 31, 41 mounted on respective instruments 100, 200, 300, 400 and a display device 2 conducting display of the image data thereof is conducted by using an ID number allocated in advance to each of them makes it possible to conduct displaying from a prescribed imaging device 11, 21, 31, 41 adequately and accurately, without causing wire crossing or the like, and a simple and inexpensive ophthalmic examination and treatment system can be provided.

By employing wireless devices (wireless CCD cameras) as the imaging devices 11, 21, 31, 41 mounted in appropriate positions on such ophthalmic medical instruments 100, 200, 300, 400, it is possible not only to resolve the conventional problems such as a restriction placed on a mounting position on the main instrument, but the imaging devices 11, 21, 31, 41 will also be capable of imaging necessary sites as the objects of imaging, thereby exhibiting their functions to the fullest.

Moreover, since wireless imaging devices 11, 21, 31, 41 are employed, cables for connection with the display device 2 and recording device 6 are unnecessary, and since the primary instruments (ophthalmic medical instruments) 100, 200, 300, 400 and the wiring thereof will not be a hindrance, a user-friendly imaging system can be constituted. Further, the ophthalmic medical instrument 2, which is the primary instrument, can be transported freely, as necessary. When transporting the primary instruments 100, 200, 300, 400, only the imaging device 11, 21, 31, 41 need to be mounted, and there is an advantage in that the display device 2 and recording device 6 may be located at the place of permanent installation, and necessary imaging may be conducted with certainty.

Another advantage of the above-described configuration is that an ophthalmic examination and treatment system 1 can be obtained which makes it possible to improve the usability of the wireless imaging devices 11, 21, 31, 41 mounted on the ophthalmic medical instruments 100, 200, 300, 400, to simplify the relationship with the display device 2 and recording device 6 thereof, and to improve the overall user-friendliness.

Here, FIG. 2 and FIG. 3 illustrate examples of the slit lamp 100 employing the present invention. The slit lamp 100 comprises an eyepiece tube 13, a beam splitter 14, a loading portion 15 for various internal filters, and a stand 16 onto which the above components are mounted. Also, the imaging device 11 is mounted in an appropriate position.

The configuration of the wireless CCD camera, which is the aforementioned imaging device 11, is such that it is capable of sending image signals to a plurality of display devices 2 (three devices in this example) provided at suitable locations separate from the position in which the instrument 100 is provided, and suitably displaying such image signals.

The slit lamp 100 of such a configuration can be moved to any position, and is capable of transmitting images to the display devices 2 provided at separate locations by wireless communication in a simple and reliable manner.

FIG. 4 shows an example in which an eyepiece of the slit lamp 200 serves as an ophthalmic medical instrument. Here, the stand of the instrument is omitted. It goes without saying that with the imaging device 21 such as a wireless CCD camera mounted on such an eyepiece, transmission of signals to a corresponding display device (not shown in the figure) and reception of signals therefrom can be also adequately conducted by attaching an ID to the signal from the transmission/reception unit 22.

Referring to FIG. 5, the imaging device 31 composed of a wireless CCD camera is mounted on the operation microscope 300 used, for example, when performing ophthalmic surgery, thereby enabling the surgery appropriate at the time of ophthalmic examination and treatment to be conducted in a simple manner, while viewing via the microscope 300.

Here, the reference numeral 33 stands for a variable-power microscope, 34—a spare lamp unit, 35—a stand, and 36—a grip portion.

It goes without saying that the aforementioned operation effect is also obtained when applying the present invention to such a variable-power microscope 300.

FIG. 6 is a schematic view of a chart management system as an example of the ophthalmic medical instrument 400 in the ophthalmic examination and treatment system 1 according to the present invention.

As described in a simple manner hereinbelow, the chart management system denoted as a whole with the reference symbol 40 comprises a wireless imaging device 41 composed of a wireless CCD camera or the like which captures the charts 43, 43A created by a doctor and picks them up as images, and a chart management control unit 45 comprising a reception unit 44 which receives the images captured by the imaging device 41 as information data by wireless communication transmission.

Here, character information of the chart 43 created by a doctor by handwriting, or display information provided by the chart 43A that was created by an input into a personal computer 46 and was information displayed on a display unit 46a may serve as the aforementioned charts 43, 43A.

The chart management control unit 45 comprises an operation control unit 47 for controlling the wireless image device 41 by remote operations. The reception unit 44 may be used as the transmission/reception unit. Furthermore, the chart management control unit 45 comprises a display unit 48 for displaying information data transmitted from the wireless imaging device 41. As a result, the operator can be informed about the management and control state at all times.

The chart management control unit 45 may also comprise a data conversion unit 49 for converting the image data obtained with the wireless imaging device 41 into character information data (text information). Furthermore, a data recording unit 51 is connected to the chart management control unit 45, thereby making it possible to record the information data transmitted from the chart management control unit 45 via a wire or wireless information transmission unit 52. The data recording unit 51 generally may be provided in the same location as the chart management control unit 45, but such a disposition is not limiting, and the data recording unit may be provided in a separate location.

Further, a plurality of information processing terminals 53 for receiving the information data transmitted via the wire or wireless information transmission unit 52 are appropriately connected to the chart management control unit 45. Those multiple information processing terminals 53 are disposed in advance in an accounting department, examination department, or pharmacy of a hospital for transferring the information data by an appropriate method such as wire connection by cable wiring, public communication line, or wireless communication transmission. A display unit 54 such as a monitor for displaying the information data, or an output unit 55 for print output thereof may be provided in those information processing terminals 53.

Needless to say, the operation effect identical to the above-described effect can be also obtained by using the chart management system 400 of the above-described configuration as the ophthalmic medical instrument in the ophthalmic examination and treatment system 1.

Further, the present invention is not limited to the structures explained in the foregoing embodiments, and it goes without saying that the shape and structure of the respective components constituting the ophthalmic examination and treatment system 1 may be suitably modified or changed.

For example, in the aforementioned embodiments, examples are given in which the present invention was employed in slit lamp 100, eyepiece of a slit lamp 200 and an operation microscope 300, but the present invention is not limited thereto, and, needless to say, appropriate portions may be arbitrarily modified.

Further, the transmission/reception unit that was not described in detail in the aforementioned embodiments appropriately comprises an ID forming unit or an ID storing unit for forming the own ID thereof, an ID reception unit or an ID detection unit for receiving the ID attached to the received signal, an ID discrimination unit for conducting the comparison thereof, and an ID transmission unit.

What is claimed is:

1. An ophthalmic examination and treatment system comprising:
    a plurality of ophthalmic medical instruments used in ophthalmic examination and treatment;
    wireless imaging devices mounted on respective said ophthalmic medical instruments; and
    at least one display device for displaying images captured with said imaging devices, wherein
    each imaging device comprises transmission/reception unit for conducting transmission and reception of information data with said display device by wireless communication;
    the transmission/reception unit has an inherent ID allocated correspondingly to each imaging device, transmits a data signal with the ID signal attached thereto to the transmission/reception unit of said display device, and when an ID confirmation signal attached to a control signal from the transmission/reception unit of said display device and the own ID coincide, receives said control signal; and
    the display device receives a data signal with an ID signal attached thereto from each imaging device, conducts displaying with the data signal corresponding to said ID and enables the remote control of the imaging device corresponding to said ID by attaching the ID signal and sending the control signal.

2. The ophthalmic examination and treatment system according to claim 1, wherein said display device comprises a recording device for recording the image displayed on said display device.

3. The ophthalmic examination and treatment system according to claim 1 or 2, wherein said ophthalmic medical instrument is a slit lamp.

4. The ophthalmic examination and treatment system according to claim 1 or 2, wherein said ophthalmic medical instrument is an operation microscope.

5. The ophthalmic examination and treatment system according to claim 1 or 2, wherein said ophthalmic medical instrument is a fundoscopy device.

6. The ophthalmic examination and treatment system according to claim 1 or 2, wherein said ophthalmic medical instrument is a display instrument for displaying a chart produced by a doctor by handwriting or a PC input.

7. The ophthalmic examination and treatment system according to claim 1, wherein said imaging device is a wireless CCD camera.

8. The ophthalmic examination and treatment system according to claim 2, wherein said imaging device is a wireless CCD camera.

9. The ophthalmic examination and treatment system according to claim 3, wherein said imaging device is a wireless CCD camera.

10. The ophthalmic examination and treatment system according to claim 4, wherein said imaging device is a wireless CCD camera.

11. The ophthalmic examination and treatment system according to claim 5, wherein said imaging device is a wireless CCD camera.

12. The ophthalmic examination and treatment system according to claim 6, wherein said imaging device is a wireless CCD camera.

* * * * *